United States Patent
Lin

(10) Patent No.: US 11,633,111 B2
(45) Date of Patent: Apr. 25, 2023

(54) REAL-TIME INTRAOPERATIVE BLOOD LOSS MONITORING

(71) Applicant: Alexander Y. Lin, St. Louis, MO (US)

(72) Inventor: Alexander Y. Lin, St. Louis, MO (US)

(73) Assignee: Alexander Y. Lin, St. Louis, MO (US)

( * ) Notice: Subject to any disclaimer, the term of this patent is extended or adjusted under 35 U.S.C. 154(b) by 1323 days.

(21) Appl. No.: 15/768,647

(22) PCT Filed: Oct. 17, 2016

(86) PCT No.: PCT/US2016/057387
§ 371 (c)(1),
(2) Date: Apr. 16, 2018

(87) PCT Pub. No.: WO2017/066783
PCT Pub. Date: Apr. 20, 2017

(65) Prior Publication Data
US 2018/0266870 A1    Sep. 20, 2018

Related U.S. Application Data

(60) Provisional application No. 62/242,739, filed on Oct. 16, 2015.

(51) Int. Cl.
| | |
|---|---|
| A61B 5/02 | (2006.01) |
| A61B 46/20 | (2016.01) |
| A61B 50/00 | (2016.01) |
| A61M 5/00 | (2006.01) |
| A61M 5/168 | (2006.01) |
| A61M 5/14 | (2006.01) |
| A61M 1/00 | (2006.01) |

(Continued)

(52) U.S. Cl.
CPC .......... *A61B 5/02042* (2013.01); *A61B 46/20* (2016.02); *A61M 5/00* (2013.01); *A61M 5/168* (2013.01); *G01F 22/00* (2013.01); *G01G 17/04* (2013.01); *G01G 19/414* (2013.01); *A61B 50/00* (2016.02); *A61F 13/36* (2013.01); *A61M 1/60* (2021.05); *A61M 1/777* (2021.05); *A61M 3/02* (2013.01); *A61M 5/14* (2013.01); *A61M 2205/6072* (2013.01)

(58) Field of Classification Search
CPC ...... G01F 22/00; G01G 17/04; G01G 19/414; A61B 5/02042; A61B 5/14; A61B 5/00; A61B 5/168; A61B 46/20; A61B 50/00; A61M 1/777; A61M 3/02; A61M 2205/6072; A61F 13/36
See application file for complete search history.

(56) References Cited

U.S. PATENT DOCUMENTS

| | | | | |
|---|---|---|---|---|
| 5,944,668 A | * | 8/1999 | Vancaillie | ......... A61M 5/16895 604/246 |
| 2012/0095422 A1 | * | 4/2012 | Morris | .................. A61M 1/777 340/10.1 |

* cited by examiner

Primary Examiner — Manuel L Barbee
(74) *Attorney, Agent, or Firm* — Riverside Law LLP

(57) ABSTRACT

Fluid introduction into the patient during surgery can be tracked more accurately. For example, saline is often introduced to a patient to clean an operating site. The saline is taken from a sterile bucket and introduced to the patient. In one described approach, the system senses the volume or weight of fluid in the sterile bucket and determines any decrease in the volume or weight to be an introduction of fluid to the patient. If, however, additional saline is added to the bucket, that addition is not counted in the fluid tracking and the further decrements from that new fluid amount is what is used to track fluid addition to the patient.

7 Claims, 4 Drawing Sheets

(51) Int. Cl.
*A61M 3/02* (2006.01)
*A61F 13/36* (2006.01)
*G01F 22/00* (2006.01)
*G01G 17/04* (2006.01)
*G01G 19/414* (2006.01)

REAL-TIME INTRAOPERATIVE BLOOD LOSS MONITORING

CROSS-REFERENCES TO RELATED APPLICATIONS

This application is a U.S. national phase application filed under 35 U.S.C. § 371 claiming benefit to International Patent Application No. PCT/US16/057387, filed Oct. 17, 2016, which is entitled to priority under 35 U.S.C. § 119(e) to U.S. Provisional Patent Application No. 62/242,739, filed Oct. 16, 2015, each of which application is hereby incorporated herein by reference in its entirety.

TECHNICAL FIELD

This invention relates generally to blood loss monitoring, and more specifically to blood loss monitoring in an operating room context.

BACKGROUND

Blood loss during surgery can be lethal, especially in pediatric surgery where babies have very low total blood volume to start with and can die very quickly with blood loss. Even direct blood draw measurement of hemoglobin and hematocrit is not accurate, because patients receive fluids during surgery that cause unpredictable dilution of the blood, leading to inaccurate results. Our inaccurate estimates can lead to under-transfusion or over-transfusion of blood products, both with serious consequences (i.e., death from under-transfusion because not enough blood for the heart to pump, and lungs that cannot breathe from over-resuscitation or blood transfusion reaction). The ability to accurately estimate blood loss in real time would be life-saving.

Blood loss during surgery is dangerous to all patients, from babies and children (with lower blood volumes to start with) to adults (with more ischemic heart disease sensitive to blood loss or other coagulation problems). This problem literally affects every surgery we perform, so the potential number of patients who would benefit is enormous, as it does not matter which surgical specialty is performing the surgery.

Prior art dealing with assessing intraoperative blood loss can be summarized into two types: 1) estimates based on external elements such as counting bloody "sponges" manually or by weight, and 2) estimates based on internal elements such as blood draws to assess patient's blood count in a laboratory or in a machine. External estimates, especially those based on counting sponges, are extremely inaccurate: humans cannot accurately assess how much blood is soaked in a sponge. The weighted version of the sponge has increased accuracy, but in the quick pace of an operating room, especially when a surgery is bloody, the circulating nurse has no time to quickly weigh each individual sponge; in addition multiple other blood loss sources are unaccounted. Internal estimates have improved with time, as machines now can do an "auto-count" much faster than sending a blood sample to the laboratory for a "manual count" by a human technician. In fact, more recently the ultimate extension of internal assessment has been created, with a new technology called "continuous hemoglobin monitoring" via an arterial line, but even those are not accurate because patients receive fluids during surgery that cause unpredictable dilution of the blood, and when a patient's body is undergoing stress and inflammation, fluids leak out of the bloodstream into the tissues, which makes the actual intravascular blood draw non-representative of the potential amount of fluids added to the system.

This invention solves the problem of assessing real-time intraoperative blood loss in a novel way by focusing on the external environment, identifying the unique components of the system, and putting this data together in a modular fashion that would accommodate future surgical techniques and technologies, all within the confines of a busy, critical operating room environment.

SUMMARY

This work focuses on external sources of blood loss with the insight that the net blood loss calculation requires the assessment of total overall liquids loss, subtracting out the additional fluids added to the system (irrigation fluid that is typically saline or water or other near-isotonic solutions).

The mathematical computation is (each variable is a volume):

Patient's net blood loss=blood added to the system

Total liquid loss=Blood added to system+fluid added to system

Blood added to system, which is equivalent to Net blood loss, can be re-arranged and solved by: Net blood loss=Total liquid loss−fluid added.

This approach measures the two parameters on the right side of the equation. Both total liquid loss and fluid added can have direct and indirect components. Finally, there is a modular component available for future yet-to-be-developed surgical techniques and technologies.

Various components are combined in this formula to be able to assess these components in real-time to increase safety to patients. Six such components are:
  A. Liquid loss via suctioning (direct)
  B. Liquid loss via sponges (direct)
  C. Liquid loss via indirect sources (patient's body, table, drapes, floor)
  D. Fluid addition via direct addition to the field (irrigation)
  E. Fluid addition via indirect sources (external medications or pharmaceutics)
  F. Modular surgical technologies (Cell Saver, bypass machine, future specialized technologies)

The operating room is full of disposable items necessary for sterile surgery: canisters to hold the volume of suctioned fluids, sterile sponges to sop up fluid and blood, specialized drapes and floor mats, buckets and hanging bags to add fluid to the system, and more. The Internet of Things (IoT) describes the advanced communication technology we now have at our arsenal: appropriate sensors built into objects can relay certain real-time data wirelessly to a central software server. Thus, elements analogous to What is already used in the operating room are modified by incorporating a unique blending of sensors in the equipment and the overarching computation to calculate the combination of sensor information in real-time. In other words, such a system includes both sensors (hardware) and a digital brain (software to integrate the sensor information). Keeping the workflow as close as possible to standard operating room practices improves the practicality, modularity, and extensibility of this novel invention.

In a particular aspect, fluid introduction into the patient during surgery can be tracked more accurately. For example, saline is often introduced to a patient to clean an operating site. The saline is taken from a sterile bucket and introduced to the patient. In one described approach, the system senses the volume or weight of fluid in the sterile bucket and determines any decrease in the volume or weight to be an introduction of fluid to the patient. If, however, additional saline is added to the bucket, that addition is not counted in the fluid tracking, and the further decrements from that new fluid amount is what is used to track fluid addition to the patient.

Figure 1:
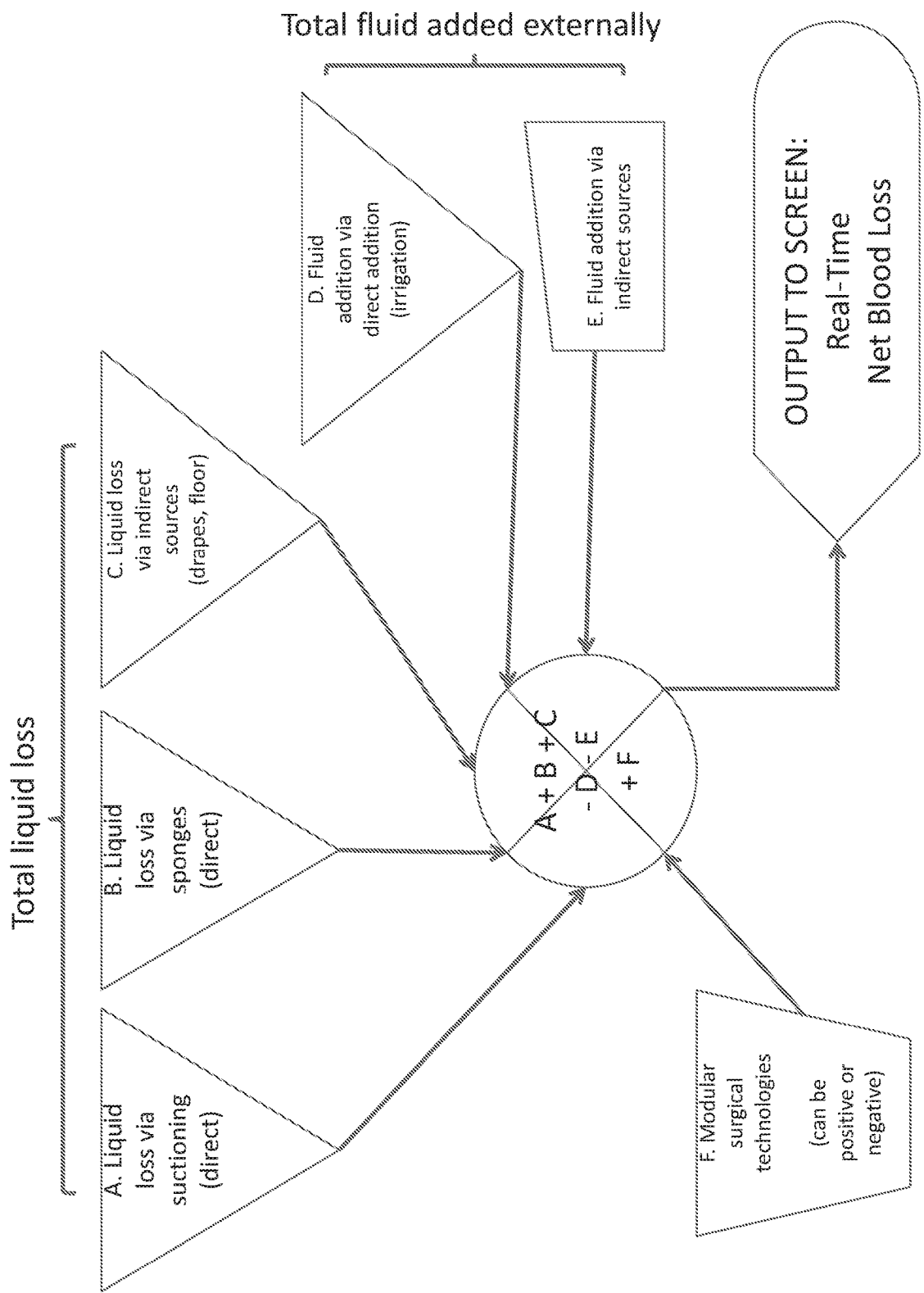
FIG. 1 is a block diagram of a system including illustrating certain processing steps according to various embodiments of the invention. In this example, the central computing device software sums the total liquid loss (from the liquid loss modules) and sums the total fluid added (from the fluid added modules), and their difference is the net blood loss. Modular surgical technologies may add to or subtract from the equation. Finally, at the end of surgery, if additional drapes, towels, mats need to be weighed, there may be a final postoperative adjustment of the estimated blood loss.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

For each of the six components described above, there are various embodiments of hardware that can be used. Regardless of the hardware embodiment chosen that is most appropriate for the hospital or center, the software remains the same, to accommodate the modularity of the hardware, and the expansibility of future yet-to-be-developed surgical technique or technologies.

Definitions

Field or Sterile Field: Area of operation that is kept sterile including patient areas not covered by drapes, tables containing sterile equipment, personnel with sterile gloves and gowns Scrub technician: person who remains sterile who hands sterile instruments or sterile fluids or sterile medications to the surgeon.

Circulator nurse: person who is not sterile, who walks around the room (i.e., "circulates") to obtain sutures, medications, bags of irrigation, and opens them sterilely to pass to the scrub tech or deposit onto the field.

Sponge: any type of cloth or absorbent material used to clean up the field, or hold pressure over a bleeding area. These are necessarily counted at the end to prevent accidentally leaving a sponge in the patient.

Drapes: The patient's operative site is "prepped" to become a sterile working environment, and drapes are placed over the entire rest of the patient to wall off the non-prepped, non-sterile areas. Modern drapes usually have adhesives to aid in segregating the sterile area from the non-sterile areas.

Prep: Preparing a patient, or prepping a patient, means cleaning the surgical site with betadine, chlorhexidine, or other cleaning agent, so that it becomes part of the sterile field.

Internet of Things (IoT): Physical sensors built into objects that can relay certain real-time data wirelessly to a central server Integrated Computing Assets Certain computing device assets allow integration of all the IoT sensor information, integrates this information via calculations, and returns the real-time estimate of blood loss as a simple number, that can be displayed on a monitor just like an OR monitor displays heart rate and other vital signs.

FIG. 1 diagrams the workflow of the software based computing assets. Net blood loss=total liquid loss−total fluid added. Each of the key six components above is represented in the diagram. This software is completely modular, as each component can be improved on with future sensor technology, additional components can be added with future surgical technology, and manual volumes can be entered as well if needed.

Hardware for Sensing Physical Factors

Figure 2:
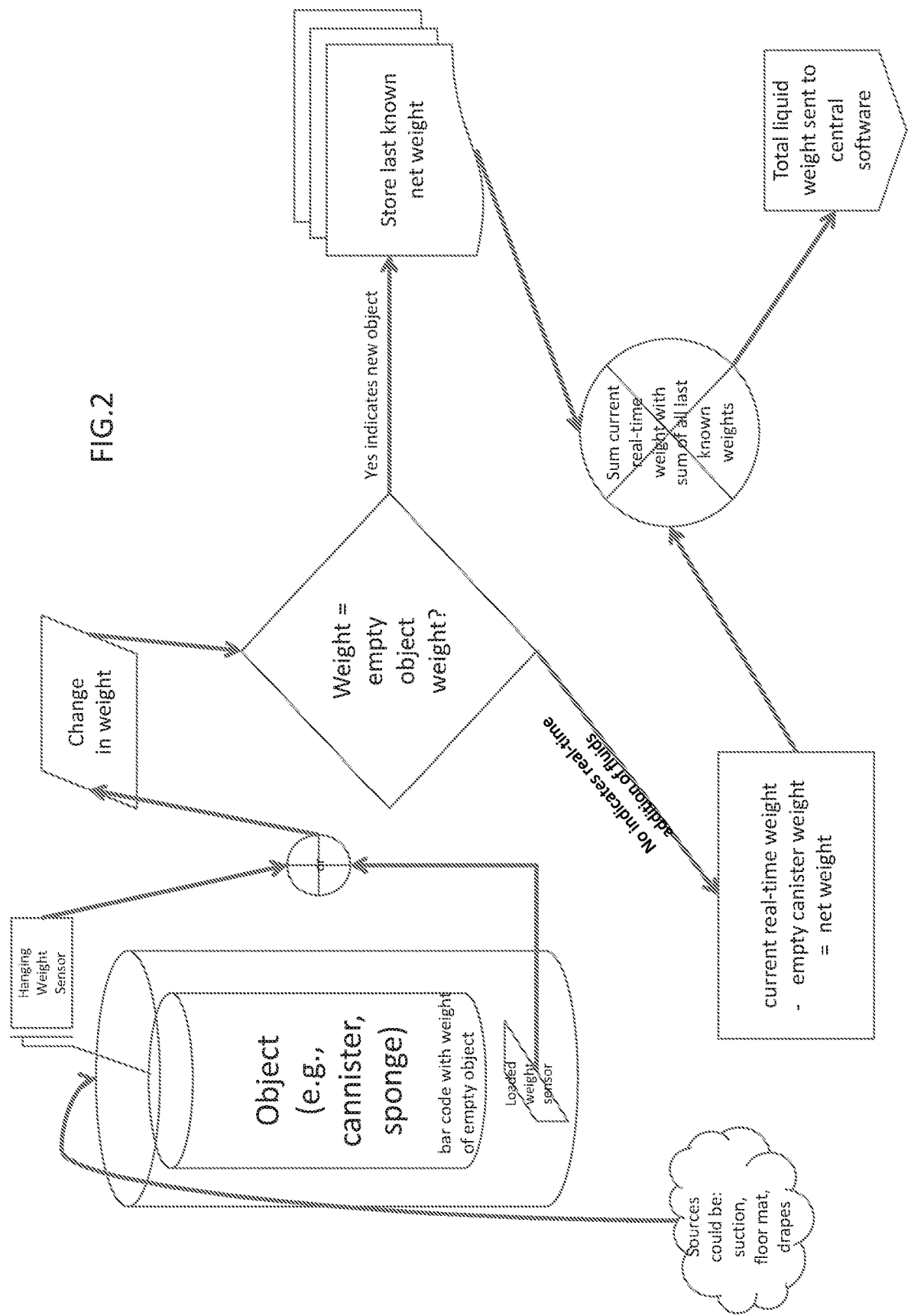
FIG. 2 is a block diagram of a system including illustrating certain processing steps according to various embodiments of the invention. This example represents the schema for objects that are continually measured in the system. Examples could be suction canisters (that are switched to new ones when full). As the canister gets filled by field suctions, floor mat suctions, or drain suctions, the weight sensor could be either a hanging weight sensor or a loaded weight sensor. The canister's weight could be entered manually or automatically by bar code. The change in weight is constantly being monitored to know the net fluid (subtracting the canister's empty weight), and when a brand new canister is switched, it knows to start the net weight all over again. Previous net weights are stored, and therefore the real-time net weight can be reported, no matter how many times the canister is switched to a new one.

FIG. 2 diagrams the standard weight sensor for real-time measuring losses. "Object" can represent a canister, a sponge. Its weight can be either measured by a loaded weight sensor, or a hanging weight sensor. The object's untouched weight is known (discussed below for various embodiments to know the weight manually or automatically via bar code). Therefore, a change in weight indicates increase in fluid loss, where the net fluid can be calculated by knowing the object's untouched weight. If the weight goes to "zero" (the object's untouched weight), it indicates a new object (such as a canister) and the last known net weight is stored (in sensor or in central software).

Six components of the hardware are described below:

A. Liquid Loss Via Suctioning (Direct)

In a typical operating room, suctions are utilized on the sterile field that are connected to suction hose that is long enough to traverse the field to a non-sterile bucket, also known as a vacuum canister. When the canister is near full, the circulator nurses switches a fresh canister to the system. The volume in the canister represents the liquid loss via suctioning. By incorporating weight sensors that transmit the actual weight via IoT, the real-time liquid loss via suctioning is always known.

Various embodiments for the sensor can be used, e.g., one that senses the weight at the bottom of the canister or one that senses the weight from the canister pulling on a hanging scale sensor. Either sensor is reasonable, and there may be other sensors developed in the future to assess the canister's weight. The central computing device is aware of the weight of an empty canister, to subtract from the total weight, to isolate the weight of the volume inside the canister. When an old filled canister is switched for a new empty canister, the sensor notes the weight went back to empty state, which allows the central computing device to know a new canister is being filled and weighed. The central computing device keeps tracks of these transitions and the sum total, to keep a real-time estimate of total volume of suctioned liquids.

B. Liquid Loss Via Sponges (Direct)

Sponges are necessary to sop up or wipe away excess blood and fluid, or to pack a bleeding area to hold pressure. Multiple sizes of sponges are available, from small "raytecs" shaped like gauze, to "lap sponges" that are larger. They are always absorbent, and they always have a piece of material built-in that is visible on X-ray (radiopaque). This is necessary to reduce the risk of leaving a foreign material (sponge) inside a patient. Because it is a preventable problem, sponges are carefully counted during surgery multiple times to ensure the "count is correct". If the count is incorrect, X-ray may be able to localize the missing sponge in the patient.

When sponges are added onto the field, they are typically added in a package of 10 sponges, and are counted aloud (to prove the package contains 10 and only 10 sponges), and written on the whiteboard for record. Each time a package is opened, it is verified and the whiteboard is updated. This provides the "correct count".

There are two main counting system for sponges. The classic method is by repeatedly counting. There are various methods to speed up the process of counting. One common equipment is a large hanging bag that contains many pockets (sort of like a closet organizer for shoes that contains many shoe pockets), so that as sponges are thrown off the field, the circulator nurse places one in each pocket. This grid of pockets makes it fairly easy to visually count how many sponges have been retrieved so far.

A second more advanced way of counting sponges has been marketed and used in some ORs. When each package of 10 sponges is opened, there is a large bar code representing the 10 sponges and there is a scanner, much like a supermarket scanner. The scanner knows this bar code represents 10 smaller codes. Each sponge actually has one of the smaller codes on it, so as they are retrieved, each one is scanned. This scanner keeps track of the sponges, rather than a manual whiteboard.

The weight of each sponge therefore represents liquid loss from the patient. Counting sponges is more complex, and there are multiple embodiments of how to keep track of the number of sponges, and their weights, and know their original non-soaked weights to subtract out, resulting in net liquid soaked in the sponge. Four embodiments are described here:

1. The lowest tech method would be to identify the sponge (to know its non-soaked weight), literally weigh it on a scale, and manually enter the weight, and the type of sponge so that the software can subtract out the weight of the sponge (see below for manual option in this invention).

Figure 3:
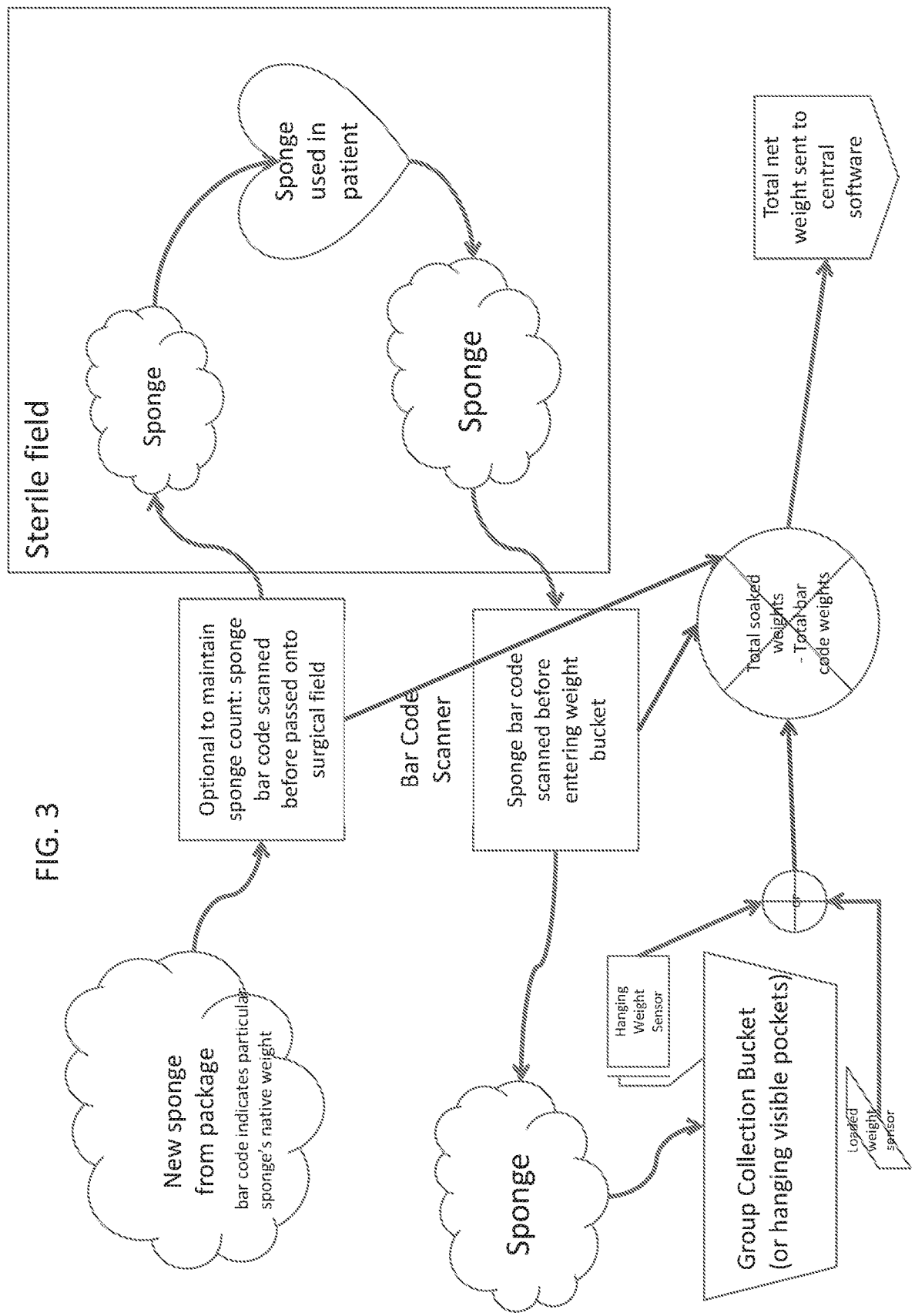
FIG. 3 is a block diagram of a system including illustrating certain processing steps according to various embodiments of the invention. Two example embodiments of sponge weighing are illustrated in this figure. The bar code contains the weight of the unsoaked sponge, no matter what sponge size, and this information is captured as the sponge is scanned into the field. After any sponge leaves the field, it needs to be scanned as they leave the field in a different order than entering—this used sponge can then be placed into a single bucket tabulating the cumulative weight of used sponges, or in the hanging visible pockets version described above (the bucket version would most likely use a loaded weight sensor, and the hanging visible pockets version would most likely use a hanging weight sensor). Given the known scanned weight of the unused sponges, and the current actual weight of the soaked sponges, the net difference is the net liquid absorbed by the cumulatively used sponges. The first bar code scan as the sponge enters the field is not absolutely necessary for real-time blood loss monitoring, however this system doubles as an automatic sponge counter if the sponge is scanned on the way into the field.

FIG. 3 demonstrates the following:

2. A automated version would be to have an identifying bar code on each sponge that identifies the type of sponge and its corresponding original non-soaked weight. As each bloody sponge is passed off the field, it is scanned and dropped into a bucket that has a weight sensor relaying via IoT. This scanner reads the sponge's original weight, then the weight sensor gets the actual weight, and the subtracted difference is the liquid in the sponge. The sponges could simply be scanned and piled onto the weight sensor, without a need to separate the sponges, as the sensor software can cumulatively track each sponge's scanned information. This is similar to the newer self-checkout lines in supermarkets where you check out each item into a plastic bag that sits on a scale, and the items are programmed by their weights, so that the self-checkout line knows if there are additional unpaid items on the scale. Finally, the scanner will also be tracking the number of sponges.

3. For ORs that wish to use the grid of visible pockets to count, the grid could be hung onto a weighted sensor that senses the weight of the pull of the pockets. Again, each sponge would have a tag identifying its non-soaked weight, and it would scan as it gets placed into a pocket. This is redundant in that the scanner is counting the sponges already, so there is no need for visual inspection, but some ORs may prefer a visual count as a backup, as many ORs are used to this system.

4. It is possible that future sensor technologies can be devised that can sense the amount of liquid a piece of fabric holds. There are already IoT sensors available that can be placed at the edges of windows that can sense if moisture has penetrated the edges. There is already a quantification curve associated with this moisture sensor, and in the future this curve may be precise enough to directly sense how much volume of fluid the sponge is holding, without the need to weigh it. In that embodiment, the sensor would still relay the volume information via IoT to the software of this invention.

Regardless of which embodiment chosen, the liquid loss via sponges' information would be tracked in real-time, and relayed to the central computing device software via IoT implementation.

C. Liquid Loss Via Indirect Sources (Patient's Body, Table, Drapes, Floor)

Once a patient's operative field is prepped, drapes are placed on the patient with adhesives, to separate the dirty areas from the prepped clean areas. Frequently towels will be laid on the field first, followed by the drapes, so there are two layers before fluids reach the patient. Minimal amount of fluid should be able to seep under the edges of the drapes, and for the most part this is negligible loss. We will discuss an embodiment below (#6) to account for this extra fluid if necessary.

Fluids can spill onto the floor. There are specialized drapes that contain pockets that then connect to suction, but these are only used in specialized cases such as head surgeries, and even then irrigation can spill off of the drapes, missing the pockets, onto the floor. Three embodiments are described below to capture the indirect fluids on the drape and floor:

1. Floor mat that exceeds the boundaries of the operating room table, that is connected to a vacuum suction that suctions excess fluid into the same vacuum canister as Hardware A, thus accounting for the volume of liquid loss via. Hardware A (losses due to suctioning). The material of the floor mat could be an absorbable surface that the surgical team is standing on, so that the superficial surface is fairly dry, and that majority of it is diverted to the suction canister.

2. The drapes can have a wide boundary that is more likely to collect fluid without overspillage onto the floor. It can similarly be made with a suction at its lowest point, collecting the drainage to the suction canister that is accounted for via Hardware A (losses due to suctioning).

3. The floor mat could be designed with a weight sensor as well, that knows its untouched weight in real-time. When personnel are standing on it, it far exceeds any known amount of fluid spillage (anything greater than 10 kg would be extremely unlikely to be anything else than a human body or partial body weight, as it is unlikely to spill 10 L of fluid all at once in a surgery; however this threshold can be adjusted depending on the type of surgery). Therefore, when all personnel are not on the pad, the actual fluid weight would register and be sent to the central computing device. When there are people on the mat, this far exceeds normal fluid loss, and the weight would be suppressed and not sent to the central computing device. It is possible that the design of such a floor would require additional technologies such as a minimally raised platform to hold the entire floor drape, in order to accommodate weight of a large surface area.

4. The drapes could also be designed to have weight sensors at their bottom so that the inferior-most ring feels the pull of the liquid weight. This weight sensor would transmit real-time weight of fluids collected in the drapes.

5. A combination of the above may be used: for example, both drapes and floor sensors could be used, so that the floor captures overspillage. Within each one, the weight sensor method and the vacuum suction method could be used. If using suction method only, can merge the suction tubing into the regular suction of Hardware A. If using both weight-based and suction based simultaneously, would have its suction go into a separate canister to avoid double-counting the volume; in this scenario the suction volume would be a checksum on the weighted volume.

6. A final embodiment involves manual weights of each item in the system: the drapes, the floor mats, the towels underneath the drapes that might experience soak-through if the drapes were not sealed adhesively well enough. This could be manual entry of the untouched weights of these items, so that the final weights can subtract out the untouched weights to get net weight. Alternatively, each item could have a scannable bar code denoting its original untouched weight, and added to the final weight pile (via Hardware B, embodiment #2). Because this method would be used after surgery is over (as it contaminates the entire field to remove the drapes), this method is no longer real-time, but likely negligible source of volume loss, so it would be acceptable to get this final weight after surgery.

D. Fluid Addition Via Direct Addition to the Field (Irrigation)

Figure 4:
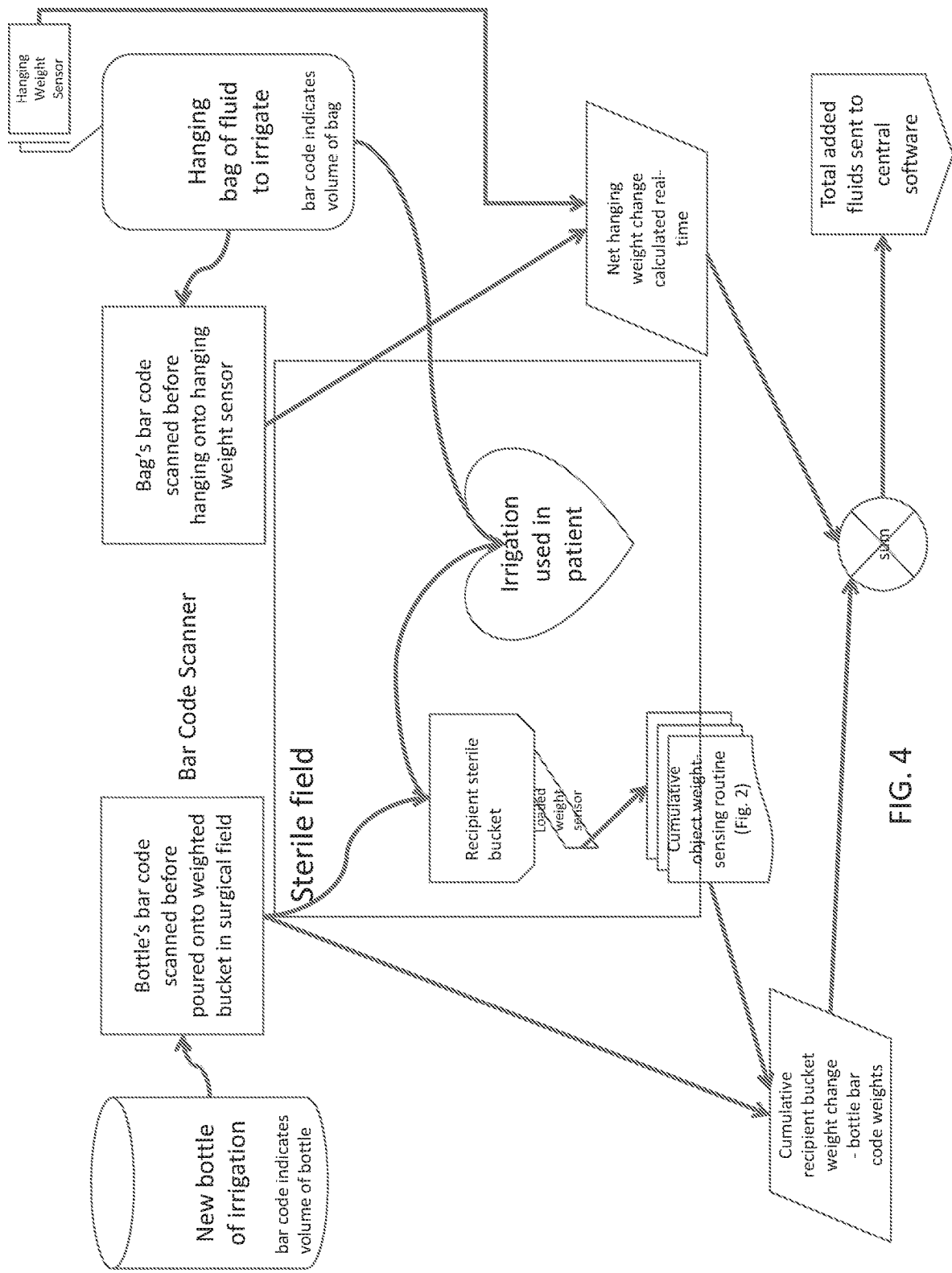
FIG. 4 is a block diagram of a system including illustrating certain processing steps according to various embodiments of the invention. Two main forms of adding fluid to the system are shown in this example. On the right, a hanging bag of irrigation fluid can have a bar code scanned as it is hung, or the hanging weight sensor can be programmed similarly to FIG. 2 where it senses each new bag when it transitions from 0 weight to a new bag's weight. After the irrigation fluid is used, then the remaining net weight difference indicates the fluid added to the system from the hanging bag. For bottles of irrigation passed onto the field: they can similarly be bar code scanned as they enter the field for the actual volume of fluid, or the recipient sterile bucket can be programmed similarly to FIG. 2 to recognize a change in weight from 0 to a common bottle volume weight. As fluid is transferred from sterile bucket to patient via basters or syringes, the weight drop is registered in a manner similar to FIG. 2 to account for repeated additions of new bottles of fluid.

Fluid addition is usually via irrigation, and plays a significant portion of the equation. Amounts are usually added in one liter increments, but any amount can be added. There are two typical modalities of addition: bottles (500 mL or 1 L typically) opened and poured into a sterile bucket on the field, or bags of fluid hung (3 liters or more typically). Then, aliquots from the sterile bucket are transferred, either via syringes or basters or cups. There are multiple embodiments to assess this fluid addition volume. FIG. 4 demonstrates one system where two embodiments run simultaneously.

1. The main bucket that receives fluids (whether directly from a circulator nurse opening a bottle, or from another machine) contains a real-time weight sensor. When fluid is added to the bucket, the sensor would always sense an increase in weight, which is recorded in the software, but not yet calculated in the final equation. When fluid is then transferred from the bucket to the patient, the weight sensor experiences a loss of fluid—this negative change in weight/volume is now interpreted as a true fluid addition to the field. If that syringe was not completely transferred to patient, it would then be advisable to use the entire syringe onto the patient (or onto the floor mat) so that all the fluid is used up, as returning the unused fluid to the sterile bucket could be interpreted as an addition to the system, when it is not.

2. A hanging bag is hung onto a hanging weight sensor, so that when a 3 L bag is hung initially, it registers as addition to the system. After irrigation with this hung bag, whatever the remaining weight is would be subtracted out to calculate net fluid added to the system, which would be sent via IoT to the central computing device.

3. For both #1 and #2, these manual amounts could be entered (1 L bottle of saline added, or 3 L bag of antibiotic irrigation fluid hung, for example). However, this could also be automated in a system similar to Hardware B, embodiment #2. Each common irrigation item would have a scannable bar code, which the software would recognize as a fluid addition. For example, the 1 L saline bottle bar code would tell the system that a liter of saline is being added. This also improves the sterile bucket estimate, because now even if an unused syringe is returned to the bucket, the central computing device is aware that only 1 L has entered the system so far, so the difference in weight is the actual fluid added.

E. Fluid Addition Via Indirect Sources (External Medications or Pharmaceutics)

For the most part, weights from medications are negligible relative to the large amount of irrigation fluids and blood loss during surgery. However, certain surgeries have greater amounts: for example, in very bloody operations, hemostatic agents (agents that encourage blood clotting) may be used, usually in aliquots of 5 mL to 10 mL. If a specialized surgery uses large volumes of additional medications, these can be accounted for via two embodiments:

1. For very frequently used items, they can be marked with a tag that is scanned as they are opened onto the field. The tag scanned lets the central computing device know 10 mL, or 20 mL (whatever the package contains) has been added to the system.

2. For less frequently used items, the amount can be entered manually via the manual override provided by the software operating in conjunction with the central computing device.

F. Modular Surgical Technologies (Cell Saver, Bypass Machine, Future Specialized Technologies)

Subspecialized technologies exist, or will be developed in the future, that have their own system of fluid additions/subtractions. The prime example is Cell Saver, or bypass machine. There are two main ways to solve the fluid calculations: either manually enter the machine's output into the central computing device software, or develop a future sensor that reads the machines information and transmits it automatically to the central computing device software via IoT implementation.

Finally, there is a manual override mechanism: just like most software, there is manual override so that there is a way to integrate new surgical techniques or technologies employed, even before sensors are developed. This can also be used at the end of case to account for postoperative items (such as those described above for indirect sources). This allows the circulator nurse to enter exact amounts of fluid manually, much as the circulator nurse already enters details into the electronic health record (EHR) during every surgery.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus for assessing real-time intraoperative blood loss from a surgical patient during surgery in a surgical field, the apparatus comprising:
   sensing devices that measure in real-time the volume of liquid directly added to or removed from the surgical patient;
   sensing devices that measure in real-time the volume of liquid indirectly lost by the surgical patient; and
   a computing device comprising:
   at least one communication port configured to receive information in real time from the plurality of sensing devices
   a processor circuit configured to process the information from the plurality of sensing devices to determine total volume of blood loss from the surgical patient by:
   summing a total liquid lost from the sensing devices that measure volume of liquid lost by the patient;
   summing a total liquid added from the sensing devices that measure volume of liquid added to the surgical patient;
   subtracting the total liquid added from the total liquid lost to determine a total volume of blood loss;
   wherein the plurality of sensing devices is capable of receiving information comprising data including: weight or volume of fluid provided to the surgical patient, number of known volumes of liquid provided to the surgical patient, weight of surgical sponges used on the surgical patient, volume or weight of fluid suctioned from the surgical field, or weight of drapes for the surgical field;
   further wherein the sensing devices that measure in real-time the volume of liquid removed from the surgical patient comprises weight sensors incorporated into surgical drapes or floor mats; wherein said drapes or floor mats are positioned underneath the patient and capable of receiving fluids from said patient, which are measured by said weight sensors to calculate the amount of said fluids.

2. The apparatus of claim 1, wherein the sensing devices that measure in real-time the volume of liquid directly removed from the surgical patient comprises weight sensors incorporated into a vacuum canister wherein the vacuum canister is capable of receiving fluids from a suction hose fluidly connected to the patient.

3. The apparatus of claim 2, wherein the vacuum canister is fluidly connected to a suction hose that is connected to a floor mat capable of receiving and diverting liquid spilled onto the floor mat from said surgical patient to said suction hose.

4. The apparatus of claim 2, wherein the vacuum canister is fluidly connected to a suction hose that is connected to a surgical drape positioned underneath the surgical patient, wherein the drape is capable of receiving fluid from the surgical patient and collecting said fluid and diverting said fluid to said suction hose.

5. The apparatus of claim 1, wherein the plurality of sensing devices comprises weight sensors incorporated into a bucket for containing and weighing at least one sponge.

6. The apparatus of claim 1, wherein the sensing devices that measure in real-time the volume of liquid added to the surgical patient comprises a weighing sensor incorporated into a container comprising fluid to be administered to the surgical patient, wherein the weight of the container after administration of the fluid corresponds to the amount of fluid added to the surgical patient.

7. The apparatus of claim 1, wherein the processor circuit summing and subtracting steps comprise:
   summing a total liquid lost using the information regarding any combination of the weight of the surgical sponges used on the surgical patient, the volume or weight of fluid suctioned from the surgical field, or the weight of the drapes for the surgical field;
   summing a total liquid added using the information regarding any combination of the weight or volume of fluid provided to the surgical patient or the number of the known volumes of liquid provided to the surgical patient;
   subtracting the total liquid added from the total liquid lost to determine a total blood loss value;
   wherein the processor circuit is further configured to sum the total liquid added by determining an amount of fluid applied from a fluid containing device to the surgical field by subtracting a sensed volume or weight of fluid in the fluid containing device from an initial volume or weight of fluid in the fluid containing device and to sense an increase in volume or weight of fluid in the fluid containing device, determine a new volume or weight of fluid after the increase, and determine additional fluid dispensed from the fluid containing device based on a decrease of fluid from the new volume or weight of fluid.

\* \* \* \* \*